(12) United States Patent
Zaiken et al.

(10) Patent No.: US 8,491,503 B2
(45) Date of Patent: Jul. 23, 2013

(54) INTRAUTERINE PRESSURE CATHETER INTERFACE CABLE SYSTEM

(75) Inventors: Eliot J. Zaiken, Belchertown, MA (US); MaryJo A. Toomey, Southwick, MA (US); Stewart W. Low, Vancouver, WA (US)

(73) Assignee: Covidien LP, Mansfield, MA (US)

( * ) Notice: Subject to any disclaimer, the term of this patent is extended or adjusted under 35 U.S.C. 154(b) by 1359 days.

(21) Appl. No.: 10/952,942

(22) Filed: Sep. 29, 2004

(65) Prior Publication Data
US 2006/0073728 A1   Apr. 6, 2006

(51) Int. Cl.
*A61B 5/103* (2006.01)
*A61B 5/117* (2006.01)

(52) U.S. Cl.
USPC ............ 600/591; 600/485; 600/486; 600/588

(58) Field of Classification Search
USPC ................. 600/484–486, 561, 591; 439/132, 439/488
See application file for complete search history.

(56) References Cited

U.S. PATENT DOCUMENTS

| | | | | |
|---|---|---|---|---|
| 3,910,257 A | * | 10/1975 | Fletcher et al. | 600/483 |
| 4,200,986 A | * | 5/1980 | Ackerman et al. | 33/556 |
| 4,408,157 A | * | 10/1983 | Beaubien | 324/712 |
| 4,689,551 A | * | 8/1987 | Ryan et al. | 324/539 |
| 4,785,822 A | | 11/1988 | Wallace | |
| 4,901,735 A | | 2/1990 | Von Berg | |
| 4,999,730 A | * | 3/1991 | Pickard | 361/59 |
| 5,193,547 A | * | 3/1993 | Evans et al. | 600/481 |
| 5,279,308 A | | 1/1994 | DiSabito et al. | |
| 5,341,812 A | | 8/1994 | Allaire et al. | |
| 5,420,512 A | * | 5/1995 | Spillane et al. | 324/539 |
| 5,452,725 A | | 9/1995 | Martenson | |
| 5,566,680 A | | 10/1996 | Urion et al. | |
| 5,568,815 A | * | 10/1996 | Raynes et al. | 600/485 |
| 5,582,180 A | | 12/1996 | Manset et al. | |
| 5,743,859 A | | 4/1998 | Wodlinger et al. | |
| 5,886,426 A | * | 3/1999 | Kim | 307/142 |

(Continued)

FOREIGN PATENT DOCUMENTS

| | | |
|---|---|---|
| EP | 0 766 946 | 4/1997 |
| EP | 0766946 | 4/1997 |

(Continued)

OTHER PUBLICATIONS

Int'l Search Report for PCT/US2005/032330, dated Feb. 20, 2006.

(Continued)

*Primary Examiner* — Rene Towa
(74) *Attorney, Agent, or Firm* — Lisa E. Winsor, Esq.

(57) ABSTRACT

An interface cable system for providing electrical interconnection between an intrauterine pressure catheter system and a monitoring system is provided. The interface cable system includes a first connector configured to provide electrical interconnection between the interface cable system and the intrauterine pressure catheter system and a second connector configured to provide electrical interconnection between the interface cable system and the monitoring system. The interface cable system also includes a plurality of conductors extending between said first connector and said second connector and a switching element for configuring the interface cable system to provide, upon operation of the switching element, a time period in which a zeroing operation of the intrauterine pressure catheter system may be performed. The interface cable system also includes an indicator for indicating that the switching element has been operated, thereby indicating that the zeroing operation may be performed during the time period.

15 Claims, 5 Drawing Sheets

U.S. PATENT DOCUMENTS

| | | | |
|---|---|---|---|
| 5,951,497 A | 9/1999 | Wallace et al. | |
| 5,984,879 A | 11/1999 | Wallace et al. | |
| 6,115,624 A * | 9/2000 | Lewis et al. | 600/376 |
| 6,231,524 B1 | 5/2001 | Wallace et al. | |
| 6,429,548 B1 * | 8/2002 | Wagner et al. | 307/118 |
| 6,462,554 B2 * | 10/2002 | Brown | 324/500 |
| 6,663,570 B2 * | 12/2003 | Mott et al. | 600/486 |
| 6,977,507 B1 * | 12/2005 | Pannell et al. | 324/534 |
| 2002/0137997 A1 | 9/2002 | Mastrototaro et al. | |
| 2003/0028075 A1 | 2/2003 | Ulmsten et al. | |
| 2004/0147847 A1 * | 7/2004 | Ng et al. | 600/485 |
| 2004/0267103 A1 * | 12/2004 | Li et al. | 600/323 |
| 2006/0073728 A1 | 4/2006 | Zaiken et al. | |
| 2008/0132106 A1 | 6/2008 | Burnes et al. | |

FOREIGN PATENT DOCUMENTS

| | | |
|---|---|---|
| EP | 0888744 | 1/1999 |
| JP | 2154131 | 6/1990 |
| JP | 3018346 | 1/1991 |
| JP | 5344955 | 12/1993 |

OTHER PUBLICATIONS

International Search Report for International Appl'n. No. PCT/US2005/032330 dated Apr. 7, 2006.

Corresponding Japanese Office Action, Application No. 2007-533522 mailed Dec. 21, 2010.

Examiner's Report No. 2 on Patent Application No. 2005292492 by Tyco Healthcare Group LP. (2 pages).

European Office Action dated Dec. 20, 2011 for European Patent Appln. No. EP 07 253 850.7.

Examination Report cited in Application No. 586603, dated Oct. 18, 2011. (3 pages).

Examination Report cited in Application No. 2,581,283, dated Oct. 12, 2011. (4 pages).

European Search Report for EP 11 00 6002 dated Nov. 15, 2011.

Examination Report dated Feb. 1, 2012, issued in counterpart New Zealand Patent Application No. 597897 . (2 pages).

* cited by examiner

INTRAUTERINE PRESSURE CATHETER INTERFACE CABLE SYSTEM

FIELD OF THE INVENTION

The present invention relates to intrauterine catheters, and more particularly, to a cable system for transmitting signals from an intrauterine pressure catheter.

BACKGROUND OF THE INVENTION

In monitoring and/or analyzing fetal contractions, externally applied devices (e.g., tocodynamometers) and intrauterine devices have been used. Regarding intrauterine pressure monitoring, catheters are typically inserted directly into the uterus (e.g., after the amniotic membranes have been broken). Once a catheter has been inserted in the uterus, a pressure measurement is taken by the catheter. The measured pressure is then transferred from the catheter (either electrically or mechanically depending on the type of catheter) to an interface cable. The interface cable then electrically transfers the pressure in the form of an electrical signal to one or more fetal monitors. A number of pressure catheter components and systems are described in U.S. Pat. No. 5,566,680 to Urion et al., the contents of which are incorporated in this application by reference.

Often, it becomes desirable to "zero" or "re-zero" the pressure catheter in situ. For example, a pressure catheter may include a pressure transducer that is "zeroed" to ensure that an output of the pressure transducer may be accurately compared to a reference value. Many conventional pressure catheters do not allow for a zeroing operation to be performed in situ. Further, the pressure catheters that do provide for such a zeroing operation suffer from a number of deficiencies. For example, in certain systems, a user depresses and holds a button on an interface cable, and then (while continuing to hold the button in a depressed state) zeroes the system through a mechanism provided on a fetal monitor. Such an operation is inconvenient because the user holds the button on the interface cable with a first hand and operates the zeroing mechanism on the fetal monitor with the other hand. Further, the user has no efficient way of knowing if the system is ready for the zeroing process to be performed.

Additionally, it is often desirable to confirm the functionality of the interface cable used in conjunction with an intrauterine pressure monitoring system. In certain conventional intrauterine pressure monitoring systems, a user follows a relatively complex multi-step process before referring to a screen of a monitoring system in order to verify if the interface cable is functioning properly. By their nature, such conventional procedures undesirably have a number of sources of potential error (e.g., errors in following a complex multi-step procedure, human error in determining if the screen indicates that the cable is functioning properly, etc.).

Thus, it would be desirable to provide an interface cable that overcomes one or more of the above-described deficiencies.

SUMMARY OF THE INVENTION

According to an exemplary embodiment of the present invention, an interface cable system for providing electrical interconnection between an intrauterine pressure catheter system (e.g., a pressure catheter) and a monitoring system (e.g., a fetal monitor) is provided. The monitoring system receives a pressure measurement from the intrauterine pressure catheter system via the interface cable system. The interface cable system includes a first connector configured to provide electrical interconnection between the interface cable system and the intrauterine pressure catheter system and a second connector configured to provide electrical interconnection between the interface cable system and the monitoring system. The interface cable system also includes a plurality of conductors extending between the first connector and the second connector. The interface cable system also includes a switching element for configuring the interface cable system to provide, upon operation of the switching element, a time period in which a zeroing operation of the intrauterine pressure catheter system may be performed. The interface cable system also includes an indicator for indicating that the switching element has been operated, thereby indicating that the zeroing operation may be performed during the time period.

According to another exemplary embodiment of the present invention, an interface cable system for providing electrical interconnection between an intrauterine pressure catheter system and a monitoring system is provided. The monitoring system receives a pressure measurement from the intrauterine pressure catheter system via the interface cable system. The interface cable system includes a first connector configured to provide electrical interconnection between the interface cable system and the intrauterine pressure catheter system and a second connector configured to provide electrical interconnection between the interface cable system and the monitoring system. The interface cable system also includes a plurality of conductors extending between the first connector and the second connector. The interface cable system also includes a test plug configured to be coupled to the first connector when the first connector is not coupled to the intrauterine pressure catheter system. The test plug may be used to determine if the interface cable system is functioning properly. The interface cable system also includes an indicator for providing an indication if it is determined that the interface cable system is functioning properly.

According to yet another exemplary embodiment of the present invention, a method of performing a zeroing operation on an intrauterine pressure catheter system is provided. The method includes providing interconnection between the intrauterine pressure catheter system and a monitoring system via an interface cable system. The method also includes operating a switching element included in the interface cable system to provide a time period during which a zeroing operation of the intrauterine pressure catheter system may be performed. The method also includes providing an indication that the switching element has been momentarily operated, thereby indicating that the zeroing operation may be performed. The method also includes zeroing the intrauterine pressure catheter system.

According to yet another exemplary embodiment of the present invention, a method of verifying the functionality of an interface cable system is provided. The interface cable system provides electrical interconnection between an intrauterine pressure catheter system and a monitoring system. The method includes coupling a test plug included as a component of the interface cable system to a connector of the interface cable system. The connector is configured to be coupled to the intrauterine pressure catheter system when the interface cable system is used to transmit a pressure signal from the intrauterine pressure catheter system to the monitoring system. The method also includes determining if the interface cable system is functioning properly. The method also includes providing, if it is determined that the interface cable system is functioning properly, an indication thereof.

DETAILED DESCRIPTION OF THE INVENTION

As used herein, the terms "zero," "re-zero," "zeroing," and/or "re-zeroing," even when used with respect to a catheter system itself (e.g., an intrauterine pressure catheter system), refer to the zeroing or re-zeroing operation of the catheter itself, the associated monitoring system, or a combination thereof. Further, with respect to the claims appended hereto, the terms "zero" and/or "zeroing" are intended to encompass zeroing and re-zeroing operations.

When measuring intrauterine pressure, the pressure is often measured as an offset with respect to a baseline. This baseline is established by zeroing/re-zeroing the catheter system. Thus, in certain systems, each time a new catheter system is coupled to the interface cable a zeroing/re-zeroing operation is performed.

Figure 1:
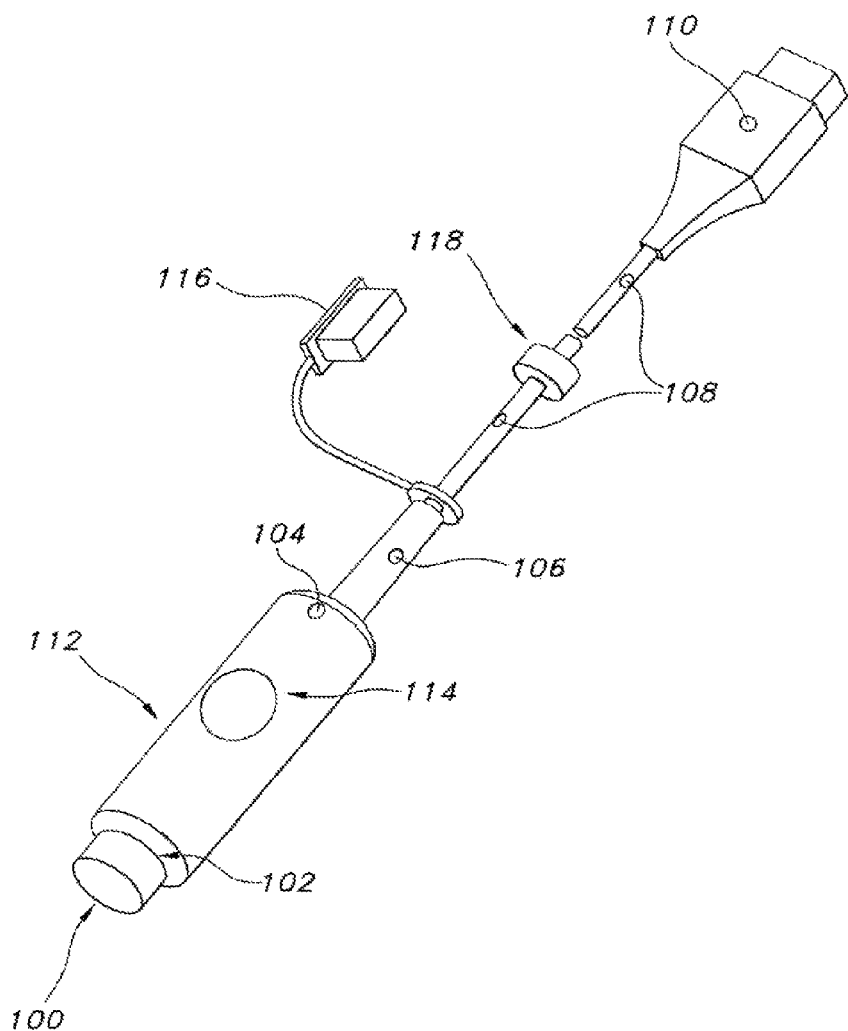
FIG. 1 is a perspective view of an interface cable system for use with an intrauterine pressure catheter according to an exemplary embodiment of the present invention.

FIG. 1 is a perspective view of interface cable system 100. Interface cable system 100 is configured to provide electrical interconnection between an intrauterine pressure catheter system and a monitoring system. The monitoring system receives a pressure measurement of the intrauterine pressure catheter system via interface cable system 100.

Interface cable system 100 includes connector 104 which is configured to provide electrical interconnection between interface cable system 100 and the monitoring system (not shown in FIG. 1). Connector 104 includes multiple pin connector 102 which is configured to be coupled to the monitoring system.

Interface cable system 100 also includes connector 110 (e.g., an overmolded connector) which is configured to provide electrical interconnection between interface cable system 100 and the intrauterine pressure catheter system (not shown in FIG. 1).

A plurality of conductors extend between connector 102 and connector 110. In the exemplary embodiment of the present invention illustrated in FIG. 1, the conductors are provided in cable 108 (e.g., a 4 wire shielded cable).

Connector 104 includes switching element 114 (e.g., a momentary switch). Through the operation of switching element 114, interface cable system 100 is configured to provide a time period during which a zeroing operation of the intrauterine pressure catheter system may be performed. For example, switching element 114 may short-circuit certain of the conductors of interface cable system 100 which carry a pressure signal from the intrauterine pressure catheter system. Such short-circuiting results in a zero potential across the signal carrying wires, which may be desired in order to perform the zeroing operation.

Connector 104 also includes indicator 112 (e.g., a light, an LED, etc.) for indicating that switching element 114 has been operated (e.g., that momentary switch 114 has been depressed). Thus, a user of interface cable system 100 has an indication that the zeroing operation may be performed. For example, such a zeroing operation may be performed by depressing a button or operating a switch on the monitoring system (not shown in FIG. 1).

Interface cable system 100 also includes strain relief 106 extending from connector 104 and leading to test plug 116 (i.e., cable check plug 116). If it is desired to test the functionality of interface cable system 100, and if connector 110 is not coupled to an intrauterine pressure catheter system, test plug 116 may be mated with connector 110. As will be explained in greater detail below, the mating of test plug 116 and connector 110 results in a test of the functionality of interface cable system 100. If it is determined that interface cable system 100 is functioning properly, an indication is provided to a user of interface cable system 100. In the exemplary embodiment of the present invention illustrated in FIG. 1, such an indication is provided by indicator 112 (e.g., a light, an LED, etc.). For example, while test plug 116 is mated with connector 110, and if interface cable system 100 is functioning properly, indicator 112 may be a continuously illuminated light or LED.

Interface cable system 100 also includes stop 118 (e.g., an overmolded knot provided on cable 108) to prevent test plug 116 from sliding or otherwise undesirably moving.

As described above with respect to interface cable system 100, an objective of the present invention is to provide an effective means by which a user/caregiver can perform a system zero or re-zero for intrauterine pressure monitoring. Another objective of the present invention is to provide a means by which the user/caregiver can verify that the intrauterine pressure catheter interface cable is performing properly.

As described above with respect to FIG. 1, according to an exemplary embodiment of the present invention, the zero/re-zero methodology utilizes a momentary switch (i.e., switching element 114) mounted on the monitor connector (i.e., connector 104), an indicator light (i.e., indicator 112), and circuitry on a circuit board enclosed inside the monitor connector (not shown in FIG. 1). When a user/caregiver momentarily presses/operates momentary switch 114 (or a button which attaches to a switch on the circuit board) signal wires configured to carry an intrauterine pressure signal are short-circuited together to create a zero voltage signal. As a result of the momentary operation of momentary switch 114, indicator light 112 flashes at a predetermined frequency (i.e., a flashing frequency) for a predetermined amount of time (i.e., a zeroing time period).

The flashing frequency can be configured in the design of the circuitry. Further, the flashing frequency may be configured such that it can not be changed by a user/caregiver. According to an exemplary embodiment of the present invention, indicator light 112 flashes at a flashing frequency of 2 hertz for a zeroing time period of 5 seconds. During the zeroing time period, the user/caregiver can properly perform a zero/re-zero operation. Further, the user/caregiver can continuously hold momentary switch 114 in a depressed state if so desired such that the zeroing time period (e.g., configured in a microprocessor not shown in FIG. 1) may be continuously restarted until the user/caregiver discontinues pressing momentary switch 114.

As will be explained in greater detail below with respect to FIGS. 2A-2B, circuitry mounted on a circuit board inside connector 104 controls the zero/re-zero functionality described above. This circuitry is powered by an excitation voltage that may be supplied by the monitoring system via multiple pin connector 102 that is electrically coupled to the monitoring system. Alternatively, an imbedded or replaceable battery could provide power for the circuit.

Using components provided in connector 104 (e.g., on the circuit board described above), the excitation voltage is directed, doubled, and/or inverted to power the appropriate components on the circuit board, which include but are not limited to resistors, op amps, an analog switch, and a microprocessor. Operation of these components is described in greater detail below with respect to FIG. 2A-2B. Briefly, the microprocessor is a controlling component, which senses when momentary switch 114 has been depressed, and then triggers an analog switch to short the two signal wires together. The microprocessor also controls the length of the zero/re-zero time period and the flashing frequency. Indicator light 112 may be mounted directly on the circuit board and can protrude through to an exterior surface of connector 104. Alternatively, indicator light may be projected to the exterior surface via a light pipe or the like.

As described above, according to an exemplary embodiment of the present invention, switching element 114 may be operated by being pushed momentarily. In contrast, certain conventional systems utilize a continuously depressed and engaged switch (i.e., in a transducer tipped catheter system). Other conventional catheter systems are actually disconnected from the interface cable (e.g., external transducer catheter systems). Because switching element 114 may be used to zero/re-zero the system through a momentarily operation (e.g., less than 1 second), the user/caregiver desirably has their hand free (where the user/caregiver's hand would otherwise be used to continuously depress a switch). As described above, once switching element 114 is engaged, it will remain engaged for the zero/re-zero time period configured in the circuitry.

During the exemplary zero/re-zero time period described above, indicator light 112 will flash for five seconds indicating that a zero/re-zero operation can be properly performed during the five seconds. For example, to perform the zero/re-zero operation, the user/caregiver presses a zero reference button on the monitoring system while indicator light 112 is flashing. Thus, the user/caregiver is provided with a predictable and reliable mechanism (i.e., the flashing of indicator light 112) which indicates that the zero/re-zero operation may be commenced.

In contrast, conventional systems do not provide any verification that a system zero/re-zero can be performed properly. As a result, if the user/caregiver does not properly prepare the system for a zero/re-zero operation (i.e., if the user does not hold down the re-zero button or engage a switch for transducer tipped catheter systems, or if the user does not disconnect the catheter from the interface cable for an external transducer catheter system) an improper zero/re-zero operation may be performed, thereby resulting in inaccurate readings. The present invention substantially reduces the possibility of the occurrence of such an improper zero/re-zero operation by providing an indication (e.g., a flashing light) that a proper zero/re-zero operation can be performed.

As provided above, certain conventional systems provide no feedback to the caregiver that a zero/re-zero operation can be performed properly. With respect to transducer tipped catheter systems that include a re-zero button or switch, the caregiver has no way of knowing whether the button/switch has been fully engaged or if it is working properly. Further, in such conventional systems, confusion often exists regarding which button needs to be pressed and held first (i.e., the re-zero button/switch on the catheter/interface cable or the zero reference button on the monitor). According to the present invention, because an indication is provided indicating that a zero/re-zero operation may be properly performed, the potential for such confusion is substantially reduced in that the indication (e.g., a flashing light) is provided only if switching element 114 has been depressed.

Certain embodiments of the present invention may provide for a zero/re-zero operation that can be easily performed with one hand. In contrast, certain conventional systems provide for the use of two hands to perform a zero/re-zero operation. For example, in the case of certain conventional transducer tipped catheter systems (having a zero/re-zero button on the interface cable), one hand is used to press and hold the zero/re-zero button while the other hand is used to press the zero reference button on the monitoring system. Certain conventional transducer-tipped catheter systems have a zero/re-zero switch on the catheter system itself, and not on the interface cable; however, such systems also use two hands to engage the zero/re-zero operation. For example, after the caregiver has pressed the zero reference button on the monitoring system, two hands are again used to disengage the switch.

Regarding conventional external transducer catheter systems, two hands are typically used to disconnect the catheter system from the interface cable. After the caregiver has pressed the zero reference button on the monitoring system, two hands are again used to reattach the catheter system to the interface cable.

Thus, in contrast to conventional systems, the present invention provides a methodology by which a user/caregiver may desirably perform a zero/re-zero operation with a single hand. According to the present invention, the user/caregiver (1) operates switching element 114 (e.g., momentary switch 114) on connector 104, (2) verifies that the system is ready for a zero/re-zero operation by noting the status of indicator 112 (e.g., flashing indicator light 112), and (3) operates the zero reference button on the monitoring system. Each of these three steps may be accomplished with one hand, thereby allowing the user/caregiver to use their other hand as desired.

As provided above, certain embodiments of the present invention relate to a system and method of verifying the functionality of the interface cable system. According to one such embodiment (as illustrated in FIG. 1), the interface cable system includes test plug 116 (e.g., a cable check plug 116 which may be embedded with female sockets), indicator light 114, and additional circuitry (e.g., provided on a circuit board enclosed inside connector 104).

According to an exemplary embodiment of the present invention, when a user/caregiver inserts connector 110 (e.g., overmolded catheter connector 110) into test plug 116, an excitation voltage from the monitoring system is transferred to the signal wires via female sockets of test plug 116 that are internally connected in such a manner that the positive voltage of the monitor is electrically connected to the positive signal voltage, and negative voltage of the monitor is electrically connected to the negative signal voltage. As a result of these connections, indicator light 112 may be continuously illuminated during the test so long as the interface cable system is functioning properly.

The circuitry mounted on the circuit board (not shown in FIG. 1) controls the interface cable system functionality check. For example, such circuitry may be powered by the excitation voltage supplied by the monitoring system via monitor pin connector 102 that plugs into the monitoring system. Alternatively, an imbedded or replaceable battery could be provided to power the circuitry. As described in greater detail below with respect to FIGS. 2A-2B, by using components on the circuit board the excitation voltage is directed, doubled, and/or inverted to power the appropriate components on the circuit board which include but are not limited to resistors, op amps, an analog switch, and a microprocessor. The microprocessor is a controlling component which continually monitors the voltage in the signal wires. When the voltage is greater than a threshold voltage indicator light 112 on connector 104 will be continually illuminated if interface cable system 100 is functioning properly. Such a threshold voltage can be selected and configured during the design of the circuitry such that it may not be changed by the user/caregiver.

According to an exemplary embodiment of the present invention, the threshold voltage is selected to be 3 volts. In such an embodiment, the maximum expected output voltage from the catheter system (i.e., a voltage signal representing an intrauterine pressure) is less than 1 volt, and as such, an algorithm configured in the circuitry can easily distinguish the threshold voltage from an actual intrauterine pressure signal.

In embodiments of the present invention utilizing both the improved zero/re-zero functionality and the improved cable verification functionality, the cable verification functionality may supercede the zero/re-zero functionality in all conditions. As a result, indicator light 112 will be illuminated continuously if the test plug is coupled to connector 110 and interface cable system is functioning properly, regardless if switching element 114 (i.e., the zero/re-zero button) has been operated.

Thus, according to certain embodiments of the present invention, indicator light 112 will be continuously illuminated when test plug 116 is plugged into connector 110 and if interface cable system 100 is functioning properly. In contrast, conventional systems typically provide no overt visual signal indicating that the interface cable is functioning properly during the interface cable check procedure. Rather, in conventional systems, a caregiver looks at the monitoring system (e.g., a screen of the monitoring system) during the interface cable test procedure to verify if the reading is in a predetermined range. This visual verification method employed in certain conventional systems follows a relatively complex sequential procedure of six steps. In contrast, according to the present invention, a simplified procedure (and a direct visual signal) is provided when the interface cable system is functioning properly.

More specifically, in contrast to the six step sequential process of conventional systems (followed by an interpretation of the reading on the screen of the monitoring system), the present invention utilizes two steps including (1) disconnecting the interface cable system from the catheter system, and (2) electrically coupling the interface cable system to the test plug. Thus, according to the present invention, a simpler, quicker, and more reliable system and method of verifying the functionality of an interface cable system is provided.

According to the present invention, by providing a visual indication related to the functionality of the interface cable system, there is less of an opportunity to improperly test the functionality of the interface cable system. This is particularly important in view of the impact of an improperly performed interface cable system check. For example, if an interface cable system is improperly tested as functioning properly, the incorrect functionality check may be followed by a multiple step zero/re-zero operation. Of course, the result of such a zero/re-zero operation is an inaccurate reading after the intrauterine pressure catheter system is reconnected to the interface cable system. Through the present invention, because of the improved reliability of the interface cable check procedure, a wasted zero/re-zero operation is not performed.

As described above, the present invention provides (1) an improved means by which a user/caregiver can perform a system zero or re-zero operation and (2) an improved means by which the user/caregiver can verify the functionality of an intrauterine pressure catheter interface cable. Details of an exemplary circuit for each of these improvements will now be described with respect to FIGS. 2A-2B.

Figure 2A:
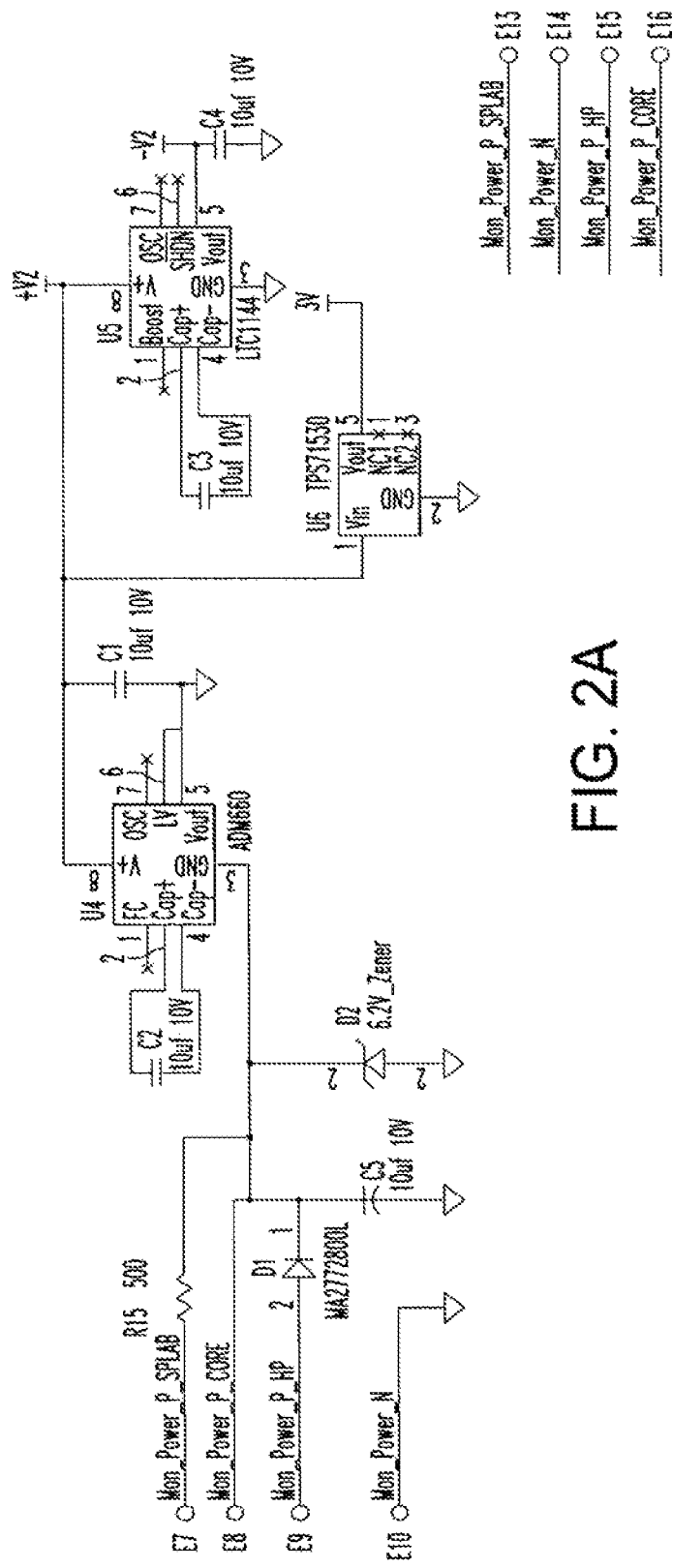
FIG. 2A is a circuit diagram of a power supply circuit included in the interface cable system of FIG. 1.

FIG. 2A is a circuit diagram of the power supply distribution of circuitry provided in connector 104 of interface cable system 100. The power supply section uses the two excitation voltage signals of the cable (coupled to terminals E7-E9 and E10 in FIG. 2A) from the monitoring system to generate the desired voltage signals. The signal coupled to terminal E10 is connected to a common "ground" of the circuits. The signal coupled to terminals E7-E9 has different paths depending on the monitor of the monitoring system to which the circuit is connected. For example, if the circuit is connected to an HP monitor the signal path from terminal E9 is connected to diode D1 which is used to transform the AC input voltage to a pulsed DC signal. Further, if the circuit is connected to a Space Labs monitor the signal path from terminal E7 is routed through resistor R15 and zener diode D2 which are used to ensure that the input level to the next stage does not exceed 7 volts. Further still, if the circuit is connected to a Corometrics monitor the signal path from terminal E8 is brought directly to the input of the next stage. Each of these signal paths leads to filter capacitor C5 which is used to smooth out the AC component of the DC signal.

The next stage (i.e., the voltage doubler stage) of the signal path leads to switched capacitor voltage doubler U4 where the input voltage is doubled. This input voltage is doubled to ensure that the supply voltage to an analog switch will be greater than the input voltage.

The output of the voltage doubler stage is fed into voltage inverter section U5 which is used to generate a negative supply voltage for the analog section of the circuitry. This negative supply voltage is desirably generated because some of the input signals are AC signals that are both positive and negative with respect to ground. The output of the voltage doubler section is also provided to linear voltage regulator U6 which provides the supply power for the microcontroller.

Figure 2B:
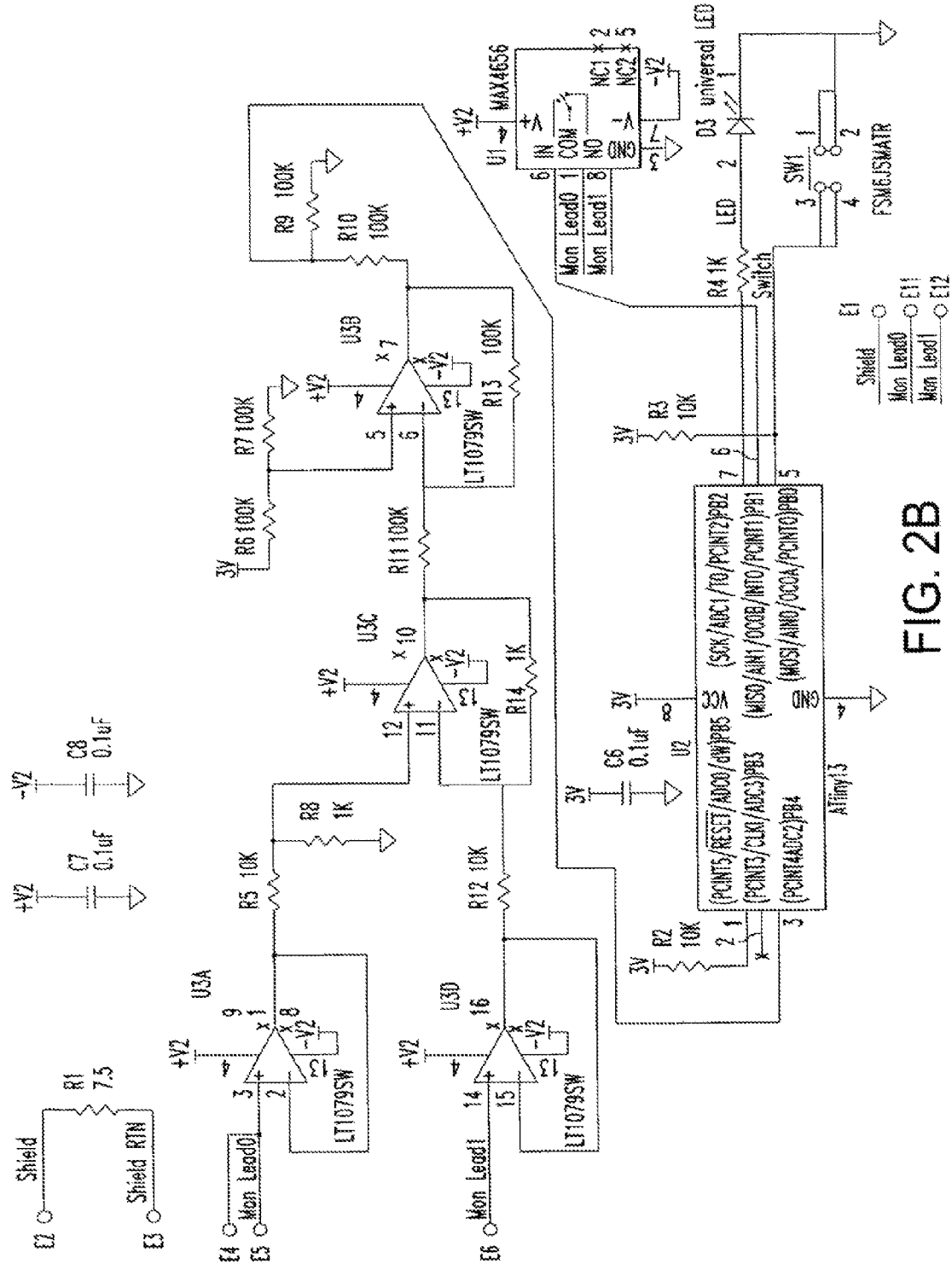
FIG. 2B is a circuit diagram of a signal processing circuit included in the interface cable system of FIG. 1.

FIG. 2B is a circuit diagram of the signal processing portion of circuitry provided in connector 104 of interface cable system 100. In the exemplary embodiment of the present invention illustrated in FIG. 2B, the signal processing portion of the circuitry uses the inner two pins of the cable provided at terminals E4, E5, and E6. The signals are transmitted through operational amplifiers U3A and U3D which are provided as a buffer. Through the use of the buffer the signals are desirably monitored without drawing enough current to substantially change the signal. From the buffer stage the signals enter summing amplifier U3C with a voltage gain of 1:10. The negative voltage gain is used to ensure that the signal level will be in a range that is acceptable to the microcontroller. The final stage U3B of the signal conditioning stage is used to level shift the signal from a positive or negative voltage to a signal between 0 and 3 volts. A voltage resistor voltage divider (incorporating resistors R9 and R10) is provided to ensure that the signal does not go above the 3V limitation of the microcontroller.

The output of the voltage resistor voltage divider circuitry is fed into an analog to digital converter on microcontroller U2 at pin 3. Microcontroller U2 determines if the value of the input signal exceeds a predetermined threshold. Microcontroller U2 illuminates an LED to alert the user/caregiver that a voltage greater than the predetermined threshold exists between input pins E5 and E6.

Input pins E5 and E6 are electrically coupled to analog switch U1, thereby allowing the two pins to be temporarily short-circuited to zero the monitoring system. Pushbutton switch SW1 is coupled to the input pin of microcontroller U2 to activate analog switch U1. If a voltage greater than the predetermined threshold voltage exists, microcontroller U2 will not drive analog switch U1. The analog signal is short-circuited for a predetermined time period by microcontroller U2.

LED D3 is driven by the microcontroller as a status indicator. LED D3 is continuously illuminated when the voltage between the input pins exceeds the predetermined threshold. When the two pins are short-circuited LED D3 is flashed off and on. Of course, the circuitry illustrated in FIGS. 2A-2B is exemplary in nature, and as such, alternative configurations are contemplated within the scope of the invention.

Figure 3:
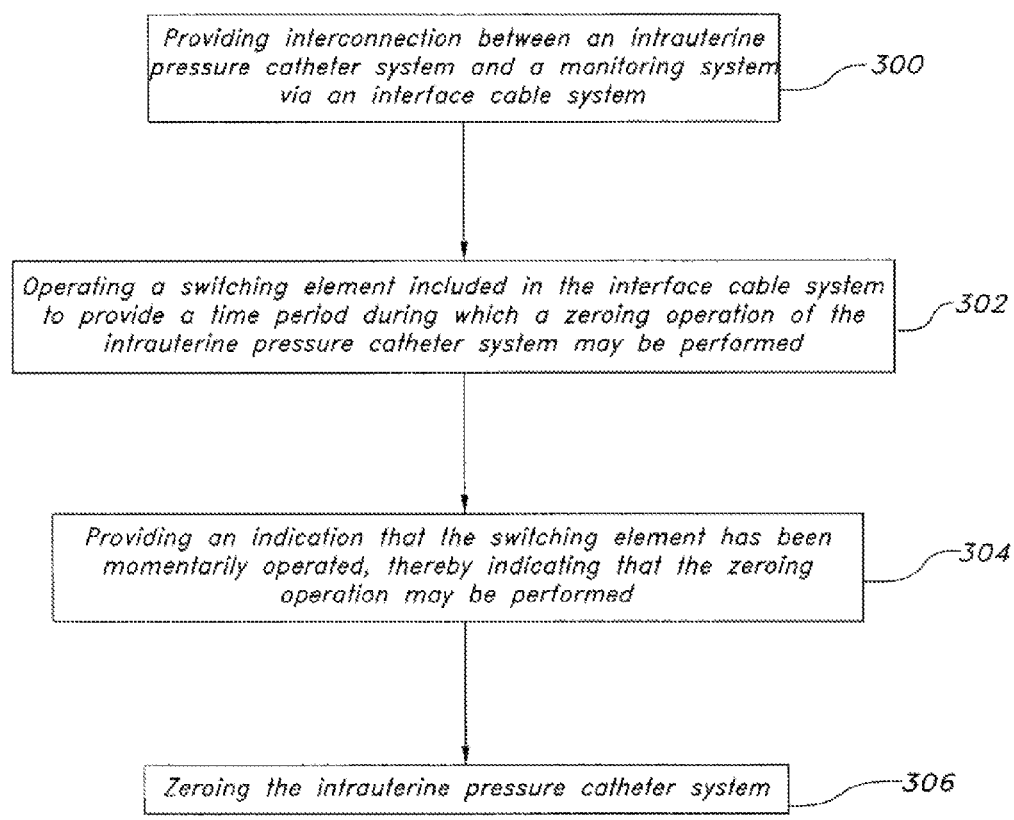
FIG. 3 is a flow diagram illustrating a method of performing a zeroing operation on an intrauterine pressure catheter system according to an exemplary embodiment of the present invention.

FIG. 3 is a flow diagram illustrating an exemplary method of performing a zeroing operation on an intrauterine pressure catheter system. At step 300, interconnection between the intrauterine pressure catheter system and a monitoring system is provided via an interface cable system. At step 302, a switching element included in the interface cable system is operated to provide a time period during which a zeroing operation of the intrauterine pressure catheter system may be performed. At step 304, an indication that the switching element has been momentarily operated is provided, thereby indicating that the zeroing operation may be performed. At step 306, the intrauterine pressure catheter system is zeroed.

Figure 4:
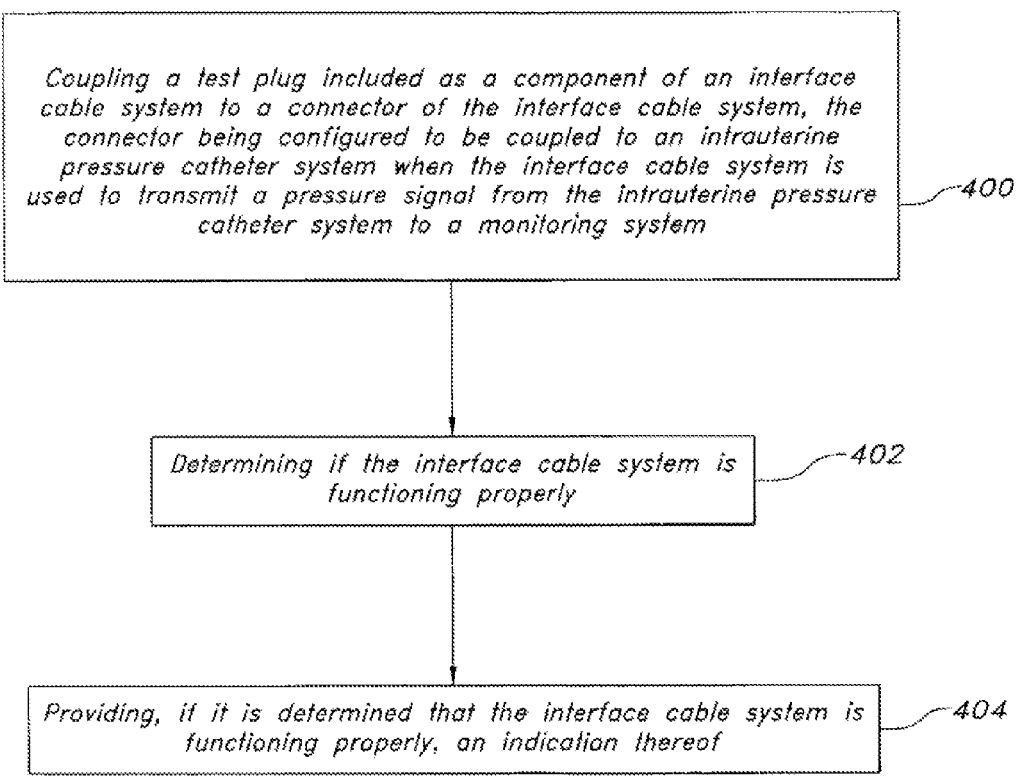
FIG. 4 is a flow diagram illustrating a method of verifying the functionality of an interface cable system according to an exemplary embodiment of the present invention.

FIG. 4 is a flow diagram illustrating a method of verifying the functionality of an interface cable system. At step 400, a test plug included as a component of the interface cable system is coupled to a connector of the interface cable system. The connector is configured to be coupled to an intrauterine pressure catheter system when the interface cable system is used to transmit a pressure signal from the intrauterine pressure catheter system to a monitoring system. At step 402, a determination is made as to whether the interface cable system is functioning properly. At step 404, if it is determined that the interface cable system is functioning properly, an indication is provided thereof.

Although the present invention has been described in terms of using a light source such as an LED as indicator 112, it is not limited thereto. Any of a number of indicators (e.g., a mechanical indicator such as a flag, an audible indicator such as a buzzer) may be used. Further, although the indicator is illustrated as being integrated as a part of connector 104, it is not limited thereto. Rather, indicator 112 may be provided at any of a number of locations included in interface cable system 100.

Although the present invention has been described in terms of the internal circuitry (e.g., the power supply and signal processing circuitry) being provided on a circuit board included in connector 104, it is not limited thereto. Rather, the circuitry may be provided at any of a number of locations included in interface cable system 100.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An interface cable system for providing electrical interconnection between an intrauterine pressure catheter system and a monitoring system, the interface cable system comprising:
    a first connector configured to provide electrical interconnection with the intrauterine pressure catheter system;
    a second connector configured to provide electrical interconnection with the monitoring system, the second connector housing power supply distribution circuitry and signal processing circuitry, the power supply distribution circuitry configured to receive an excitation voltage from the monitoring system when the second connector is coupled to the monitoring system to provide power to the power supply distribution circuitry and the signal processing circuitry, the power supply distribution circuitry being configured to generate at least one desired voltage from the excitation voltage to power the signal processing circuitry;
    a plurality of signal carrying conductors extending between said first connector and said second connector;
    a switching element configured to activate a zeroing operation of the intrauterine pressure catheter system for a period of time;
    an indicator disposed on the second connector and coupled to the power supply distribution circuitry and the signal processing circuitry such that the indicator indicates that the zeroing operation can be performed when the switching element is activated; and
    wherein the signal processing circuitry prevents the zeroing operation from being performed if an input voltage from the monitoring system exceeds a predetermined threshold voltage;
    at least one filter capacitor configured to filter out an alternating current component of the excitation voltage to generate a direct current signal;
    at least one switched capacitor configured to double the direct current signal prior to the direct current signal being provided to an analog switch and a linear voltage regulator of the signal processing circuitry, wherein the signal processing circuitry shorts at least two pins on the analog switch if the input voltage from the monitoring system exceeds a predetermined threshold voltage.

2. The interface cable system of claim 1, wherein the signal processing circuitry includes a microcontroller configured to receive power from the linear voltage regulator.

3. The interface cable system of claim 2, wherein the plurality of signal carrying conductors include at least two signal carrying conductors coupled to the at least two pins on the analog switch, wherein the analog switch is configured to short-circuit the at least two signal carrying conductors to perform the zeroing operation of the intrauterine pressure catheter system.

4. The interface cable system of claim 3, wherein the signal processing circuitry includes at least one summing amplifier coupled to the at least two signal carrying conductors, the at least one summing amplifier being configured to apply a negative voltage gain to signals provided by the at least two signal carrying conductors to generate an output signal that is in an acceptable range for the microcontroller.

5. The interface cable system of claim 4, wherein the signal processing circuitry includes a voltage divider network configured to receive the output signal from the at least one summing amplifier to ensure that the output signal does not exceed a predetermined voltage.

6. The interface cable system of claim 1, wherein the switching element is integrated with the second connector.

7. The interface cable system of claim 1, wherein the indicator includes a light source, the light source being configured to flash at a predetermined frequency during the period of time when the switching element is activated.

8. The interface cable system of claim 1, including a battery configured to provide power to the power distribution circuitry and the signal processing circuitry.

9. The interface cable system of claim 1, wherein the switching element is a momentary switch.

10. A method of performing a zeroing operation on an intrauterine pressure catheter system, the method comprising the steps of:
providing interconnection between the intrauterine pressure catheter system and a monitoring system via the interface cable system, the interface cable system comprising:
a first connector configured to provide electrical interconnection with the intrauterine pressure catheter system;
a second connector configured to provide electrical interconnection with the monitoring system, the second connector housing power supply distribution circuitry and signal processing circuitry, the power supply distribution circuitry configured to receive an excitation voltage from the monitoring system when the second connector is coupled to the monitoring system to provide power to the power supply distribution circuitry and the signal processing circuitry, the power supply distribution circuitry being configured to generate at least one desired voltage from the excitation voltage to power the signal processing circuitry;
a switching element configured to activate a zeroing operation of the intrauterine pressure catheter system for a period of time;
an indicator disposed on the second connector and coupled to the power supply distribution circuitry and the signal processing circuitry;
wherein the signal processing circuitry prevents the zeroing operation from being performed if an input voltage from the monitoring system exceeds a predetermined threshold voltage;
at least one filter capacitor configured to filter out an alternating current component of the excitation voltage to generate a direct current signal; and
at least one switched capacitor configured to double the direct current signal prior to the direct current signal being provided to an analog switch and a linear voltage regulator of the signal processing circuitry, wherein the signal processing circuitry shorts at least two pins on the analog switch if the input voltage from the monitoring system exceeds a predetermined threshold voltage;
actuating the switching element;
providing an indication that the switching element has been actuated, thereby indicating that the zeroing operation may be performed; and
zeroing the intrauterine pressure catheter system.

11. The method according to claim 10, wherein providing an indication that the switching element has been actuated occurs under a first predetermined condition.

12. The method according to claim 11, wherein the first predetermined condition includes flashing a light source at a predetermined frequency.

13. The method according to claim 10, wherein providing an indication that the interface cable system is functioning properly occurs under a second predetermined condition.

14. The method according to claim 13, wherein the second predetermined condition includes illuminating a light source.

15. The method according to claim 10, wherein actuating the switching element includes actuating a momentary switch.

* * * * *

UNITED STATES PATENT AND TRADEMARK OFFICE
CERTIFICATE OF CORRECTION

PATENT NO.        : 8,491,503 B2                         Page 1 of 1
APPLICATION NO.   : 10/952942
DATED             : July 23, 2013
INVENTOR(S)       : Eliot J. Zaiken et al.

It is certified that error appears in the above-identified patent and that said Letters Patent is hereby corrected as shown below:

In the Claims

Col. 10, line 29, delete the word "and"

Col. 10, line 36, please delete the word "signal;" and replace with --signal; and--

Signed and Sealed this
Thirtieth Day of September, 2014

Michelle K. Lee
*Deputy Director of the United States Patent and Trademark Office*